United States Patent [19]

Memberg et al.

[11] Patent Number: 4,989,617

[45] Date of Patent: Feb. 5, 1991

[54] INTRAMUSCULAR ELECTRODE FOR NEUROMUSCULAR STIMULATION SYSTEM

[75] Inventors: William D. Memberg; Paul H. Peckham, both of Cleveland Hts.; Michael W. Keith, Moreland Hill, all of Ohio

[73] Assignee: Case Western Reserve University, Cleveland, Ohio

[21] Appl. No.: 379,830

[22] Filed: Jul. 14, 1989

[51] Int. Cl.⁵ .............................................. A61N 1/00
[52] U.S. Cl. ................................... 128/785; 128/784; 128/642
[58] Field of Search .................. 128/419 P, 785, 784, 128/639, 642

[56] References Cited

U.S. PATENT DOCUMENTS

| | | | |
|---|---|---|---|
| 4,282,885 | 8/1981 | Bisping | 128/419 P |
| 4,321,931 | 3/1982 | Hon | 128/642 |
| 4,508,419 | 4/1985 | Galindo | 128/642 |
| 4,721,118 | 1/1988 | Harris | 128/419 P |
| 4,832,051 | 5/1989 | Jarvik et al. | 128/784 |
| 4,840,186 | 6/1989 | Lekholm et al. | 128/419 P |

OTHER PUBLICATIONS

"Electrical Activation of Respiratory Muscles by Methods Other than Phrenic Nerve Cuff Electrodes" by Peterson, et al., PACE, vol. 12, pp. 854-860, 1989.
*The Third Decade of Cardiac Pacing*, by Barold and Mugica, pp. 365-868, 373-374, 378-383.

*Primary Examiner*—Francis Jaworski
*Assistant Examiner*—George Manuel
*Attorney, Agent, or Firm*—Fay, Sharpe, Beall, Fagan, Minnich & McKee

[57] ABSTRACT

A helix (10) is defined by two lengths of multistrand wire (14) each surrounded by flexible, biocompatible insulation (18). A silicon elastic sheath (30) surrounds the helix and extends to a terminal end of the electrode. At the terminal end, a portion of the wire is wrapped around a periphery of the sheath to define a tissue contacting surface (34). A shaft (42) of a polypropylene anchor (40) is inserted into a hollow core (20) of the helix and thermally deformed into mechanical engagement with the helix. The anchor has a plurality of polypropylene tines or barbs (44) which firmly engage the tissue within which it is inserted but which yield for electrode removal without ripping the tissue.

15 Claims, 4 Drawing Sheets

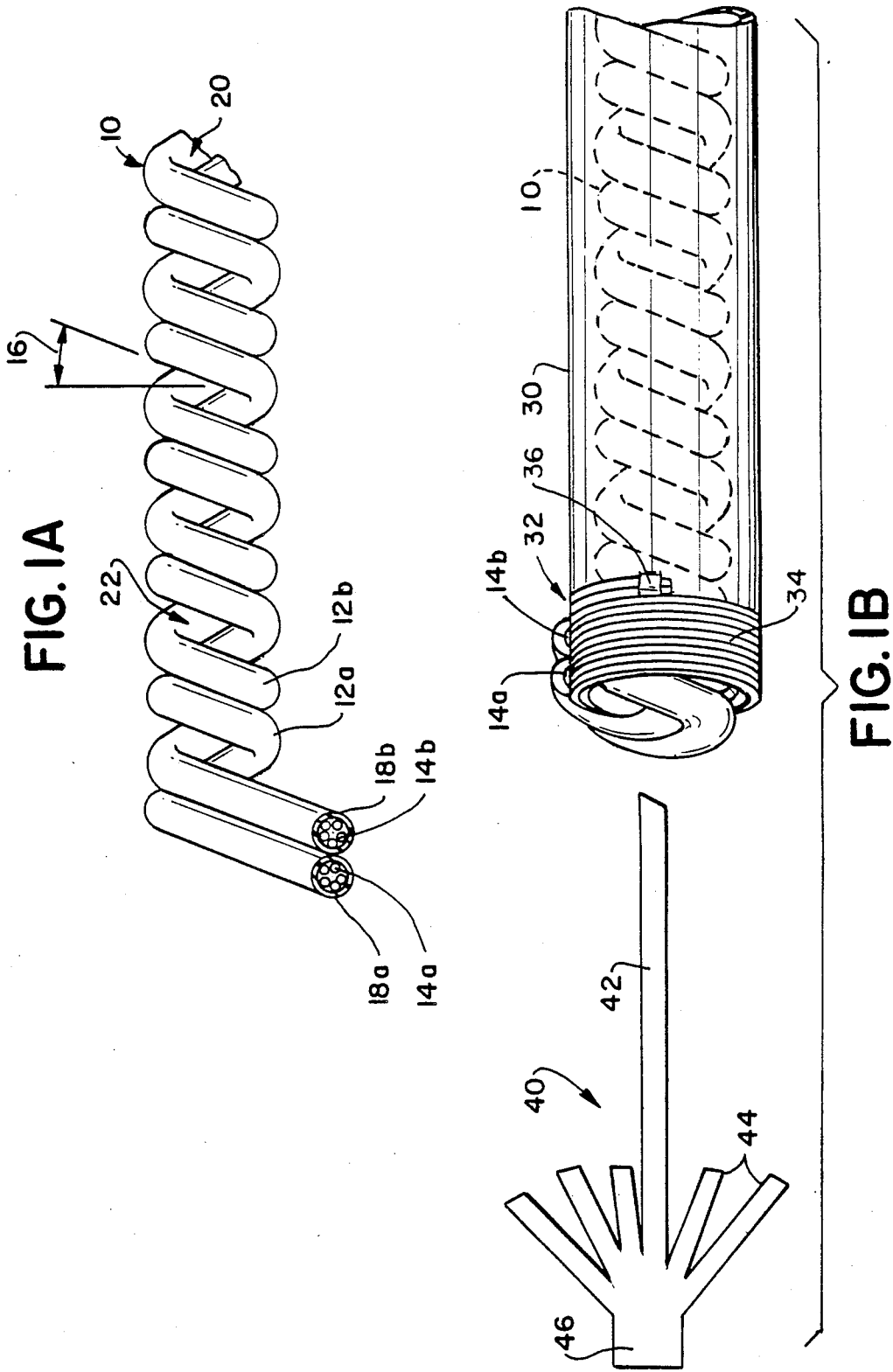

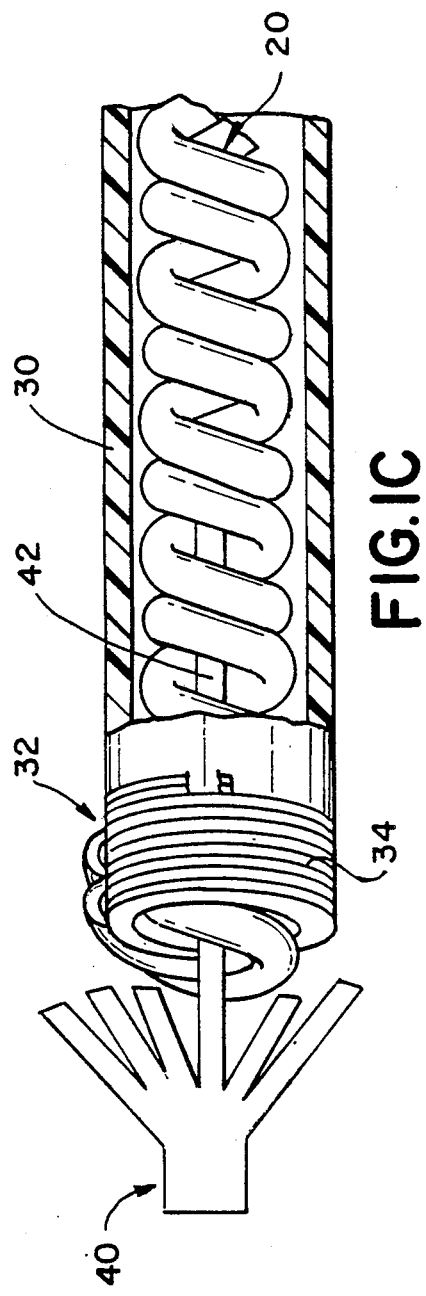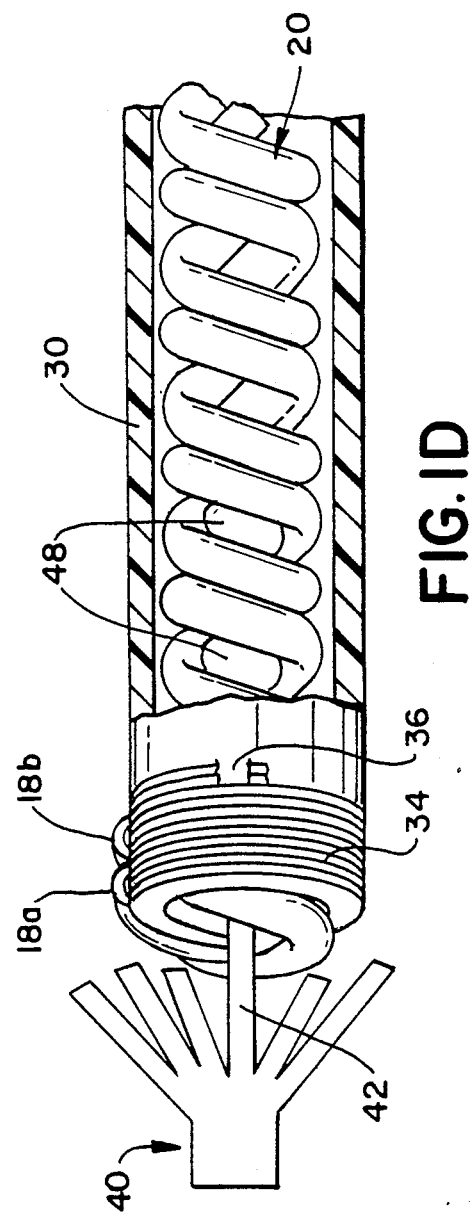

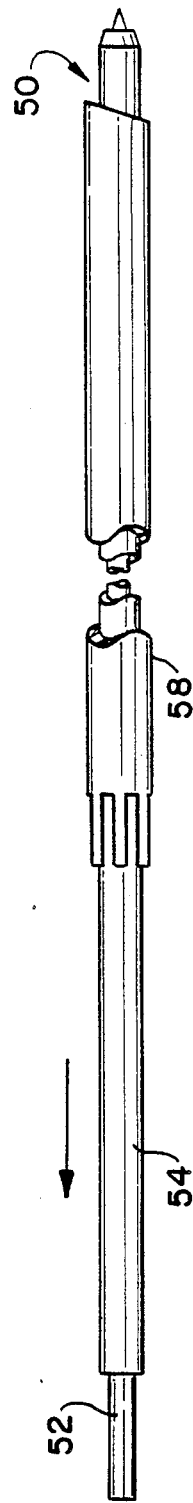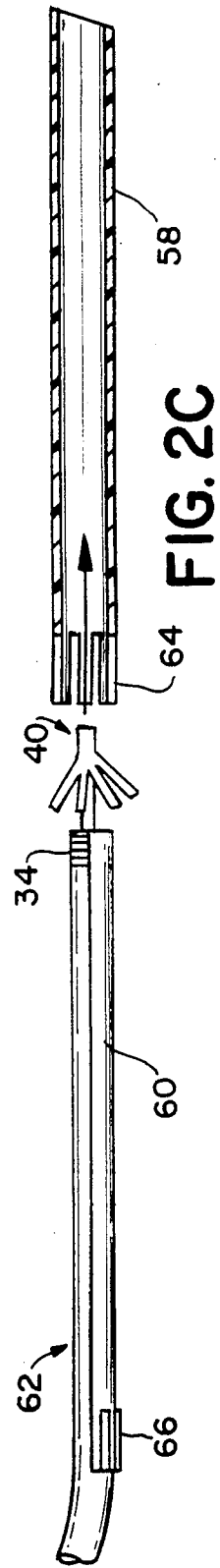

INTRAMUSCULAR ELECTRODE FOR NEUROMUSCULAR STIMULATION SYSTEM

Background of the Invention

The present invention relates to implantable electrodes. It finds particular application in conjunction with functional neuromuscular stimulation systems and will be described with particular reference thereto.

The electrodes of neuromuscular stimulation systems are commonly implanted in the muscles of a patient's arms or legs. Generally, these electrodes are different from electrodes implanted in a patient's heart in conjunction with pacemakers to accommodate the differences in the muscular tissue and the manner and frequency with which the muscular tissue contracts.

One type of neuromuscular stimulation electrode includes a length of insulated wire in which the terminal one to one and a half centimeters has been stripped to expose the electrical conductor. The electrical conductor is folded back in a sharp V to form a barb. This exposed end and the immediately contiguous lead wire are inserted into a hollow bore in the canula of a syringe-like tool and "injected" into the muscle tissue. The barb defined by folding the exposed conductor back on itself inhibits the electrode from being extracted. One of the primary drawbacks to electrodes of this type is fatigue failure of the electrical conductor.

Various electrode designs have been developed that improve upon the stripped end lead electrode. One improved electrode configuration is described in "Electrical Activation of Respiratory Muscles by Methods Other than Phrenic Nerve Cuff Electrodes", Peterson, Stellato, Nochomovitz, Dimarco, Abelson, and Mortimer, PACE, Vol. 12, pp. 854–860, May 1989, which publication is based on a paper presented at the Diaphragm Stimulation Symposium at Cardiostim '88, June 15-18, 1988. In this electrode, two Teflon coated multi-strand stainless steel wires were wrapped in a double helical pattern. At the terminal end, about the last half centimeter of the Teflon coating of the helically wrapped conductors was removed. The bare stainless steel multistrand conductors were wrapped with the same helical pattern. A colored polypropylene core was threaded through the helix and another millimeter or so beyond the end of the bare wires. A plurality of lengths of polypropylene about a half centimeter long were bundled around the exposed end of the polypropylene core. The core and the surrounding elements were inserted about a millimeter into a conforming metal tube which was heated, e.g. with a soldering iron, until the polypropylene filaments fused to the polypropylene core as barbs at the terminal end. Once injected into the muscle, muscle tissue would grow around the exposed wire coil and the polypropylene barbs anchoring it securely.

Although successful, this electrode does have drawbacks. First, fusing the plurality of polypropylene barbs to the core is difficult and labor intensive. Second, the reduction in diameter at the end of the Teflon insulation where the stripped helix of electrical conductor begins is a natural failure point. Flexing movement is focused at this point during muscular movement, eventually leading to stress failures.

The present invention contemplates a new and improved electrode and its method of construction which overcomes the above referenced problems and others.

Summary of the Invention

In accordance with one aspect of the present invention, an electrode configuration is provided in which a helix of electrical conductor is encased in a flexible plastic sheath. At a terminal, implanted end, the exposed electrical conductor is wrapped around an outer periphery of the encasing plastic sheath.

In accordance with another aspect of the present invention, at least one insulated electrical conductor is wrapped in an open core helix and surrounded by a flexible plastic sheathing. An anchor has a plurality of barbs and an elongated thermoplastic section which is received in the helix hollow core. The elongated section is thermally deformed into locking engagement with the insulated conductor helix.

One advantage of the present invention is that it anchors securely into muscle tissue.

Another advantage of the present invention is that it is resistant to stress failures of the electrical conductor.

Yet another advantage of the present invention is that it simplifies construction.

Still further advantages of the present invention will become apparent to those of ordinary skill in the art upon reading and understanding the following detailed description of the preferred embodiment.

Brief Description of the Drawings

The invention may take form in various parts and arrangements of parts or in various steps and arrangements of steps. The drawings are only for purposes of illustrating a preferred embodiment and are not to be construed as limiting the invention. The figures are illustrative of a method of constructing and inserting an electrode in accordance with the present invention and the resultant electrode in which:

FIG. 1A is a hollow core, double helical configuration of insulated multi-strand electrode lead;

FIG. 1B illustrates the hollow core, double helical configuration encased in Silastic sheathing with de-insulated ends of the electrode lead wrapped around the sheathing with a polypropylene anchor ready for insertion;

FIG. 1C is illustrative of the Silastic sheath coil, electrode end of FIG. 1C, in partial section, with the anchor inserted;

FIG. 1D is the assembly of FIG. 1C with the anchor fused to the helical electrode lead;

FIG. 2A is a probe for determining a point of insertion;

FIG. 2B illustrates sliding a metal sheath or canula over the probe and withdrawing the probe;

FIG. 2C illustrates inserting the electrode and a carrier into the metal sheath or canula after the probe has been removed;

Detailed Description of the Preferred Embodiments

Figure 2D:
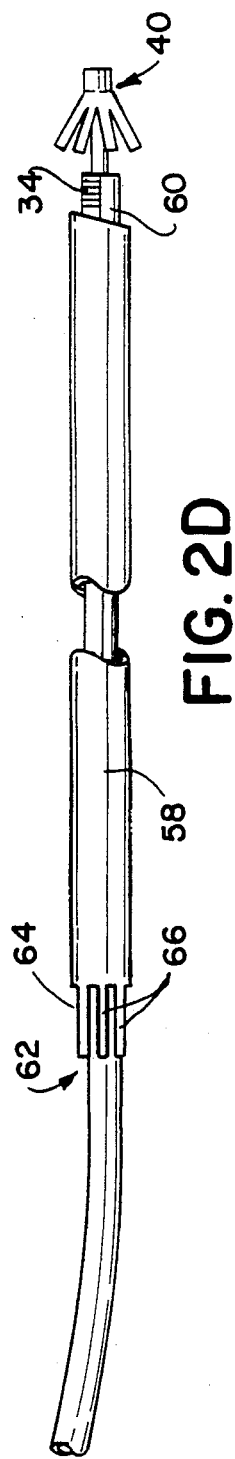
FIG. 2D shows the electrode inserted at the determined point of insertion.

With reference to FIG. 1A, a helix 10 is defined by a pair of electrical conductors 12a, 12b are wound into an open core, double helical configuration. Each electrical conductor is selected to have a relatively low electrical resistance, high mechanical strength, high ductility, high fatigue resistance, and high corrosion resistance. The preferred conductors include multistrand wire 14a, 14b Type 316 stainless steel, platinum alloys, such as platinum iridium, nickel cobalt chromium molybdenum alloys, and iron nickel cobalt chromium molybdenum alloys. The conductors are preferably seven strand wires such that the strands pack in a hexagonal close packed pattern for optimum compactness. The wire strands are wound such that they have a pitch angle 16 of about 17° relative to a plane transverse the cable axis in order to optimize tensile and compressive forces. In order to reduce electrical conductivity and increase redundancy, a third or additional conductor may be wound in the helix. However, the physical size of one or more additional conductors may necessitate increasing the pitch angle and reducing tensile or compressive strength.

The conductors 12 are insulated with a biologically inactive coating 18a, 18b which has a high tensile strength and ductility, such as TEFLON TM, polyurethane, or silicon rubber. Optionally, the strength of the cable may be improved by winding the electrical conductors around a multistrand polymeric core, such as polypropylene. However, in the preferred embodiment, the helix has an open core 20 to increase the flexibility and fatigue resistance of the electrical conductors. Further, the conductors are wound with a gap 22 between adjacent windings to accommodate compressive, tensile, and bending stresses.

With reference to FIG. 1B, the open core helix 10 is encased in a silastic silicon rubber sheath 30. In the preferred embodiment, the silastic sheathing is an open core tube within which the helix 10 is received. The sheath is preferably shrunk into firm frictional engagement with the helix. The sheathing 30 encloses the helix which prevents tissue around an implanted lead from growing into the helix. This reduces anchoring of the lead to the tissue and permits limited movement between the tissue and the lead. Optionally, in applications where greater anchoring is desirable, the Silastic sheathing may be eliminated in total or in part to enable the tissue to grow into the helix.

At a terminal or implanted end 32 of the sheathing 30, the TEFLON TM insulation 18 is removed and the de-insulated wire filaments 14 are wrapped around the exterior periphery of the silastic sheathing to define an electrically conductive surface 34 that conducts charge to surrounding tissue. The ends of the electrical conductors are fastened, such as by insertion through a segment of the Silastic sheathing 30 and sealing with silicon adhesive 36.

The length of the de-insulated wire is selected to provide a surface area 34 that delivers a charge density per stimulus pulse that is high enough to depolarize a nerve, but low enough to avoid tissue damage and electrode corrosion. This surface area is selected in accordance with the stimulus pulses to be applied and the nerve tissue to be stimulated. It will be noted that by de-insulating the electrical conductor and using the conductor itself as the electrode eliminates welds or other electrical junctions which could be subject to galvanic corrosion are avoided. Moreover, the diameter of the electrical lead windings is commensurate with the diameter of the silastic tubing, thus avoiding a diameter reduction or other point at which stresses are focused and stress failures become most apt to occur. The slight compression of the sheathing as the wire is wrapped renders the diameter of the conductive surface 34 substantially the same as the diameter of the uncompressed sheath diameter. Of course, for some applications or to facilitate production efficiency, it may be advantageous to connect the electrical leads with a separate metal element which at least in part surrounds the implanted end 32 of the sheathing.

A separate anchor 40 has a thermoplastic, polymeric shaft 42 of an appropriate diameter to be received in the hollow core 20 of the helix 10. The shaft portion and a plurality of tines 44 are anchored together in an anchor head portion 46. Preferably, the entire anchor is constructed of a polymeric material rather than a metal to avoid potential corrosion sites. Polypropylene is preferred as the polymeric anchor due to its ready availability in monofilament form and its biocompatibility. The monofilament polypropylene tines function as barbs to anchor the electrode securely, particularly while the muscle tissue is growing into firmer attachment with the electrode. However, the polymeric tines are also sufficiently flexible that the electrode can be removed surgically without the tissue damage associated with metal or rigid tines.

With reference to FIG. 1C, the polymeric shaft 42 is inserted into the hollow core 20 of the leads 12 of the helix. The polymeric shaft is constructed of a thermoplastic with a lower softening point than the sheathing 30 or the insulation 18. The terminal end of the electrode is heated such that the shaft softens and flows into gaps 22 in the helix 10 as illustrated in FIG. 1D. This flow anchors the shaft, hence the anchor to the electrode conductors 12, rendering them substantially inseparable. Moreover, the polymeric flow tends to seal the terminal end of the sheathing, limiting fluid permeability. Optionally, additional sealants may be added to inhibit biological fluids from flowing into the sheathing after the electrode is implanted.

The completed electrode is implanted into a selected point within the patient's muscle tissue. With reference to FIG. 2A, a probe 50 that includes an inner conductive rod 52 that is covered with insulation 54, except at its two ends. During surgery, an incision is made into the skin and the probe is inserted therethrough into the muscle. A source of stimulus current 56 is selectively connected with the probe to induce a contractile response in the muscle. The probe is moved or repositioned until a desired contractile response is achieved.

With reference to FIG. 2B, a metal sheath 58 is placed over the probe. The metal sheath is stainless steel tubing that has longitudinal slots cut into one end. The end of the metal sheath is positioned adjacent the end of the probe and the probe is withdrawn. With reference to FIG. 2C, the electrode is placed in a lead carrier 60, such as half circular length of tubing which is dimensioned to be slidingly received in the metal sheath 58 and to receive the lead therein. The anchor is inserted into the metal sheath followed by the lead carrier and the remainder of the lead. The lead carrier advances the lead until the electrically conductive surface 34 is at the same position as the tip of the probe (FIG. 2D). A depth of insertion gauging means 62 is provided for determining when the electrically conductive surface is in the same position relative to the inserted end of the metal sheath as was the probe. In the preferred embodiment, the depth of insertion gauging means includes a plurality of slots 64 in the metal sheath and a plurality of tabs 66 on the carrier. The slots and tabs are fashioned a coordinated length from the inserted ends of the metal sheath and carrier such that the electrically conductive surface 34 of the electrode is properly positioned.

Figure 2E:
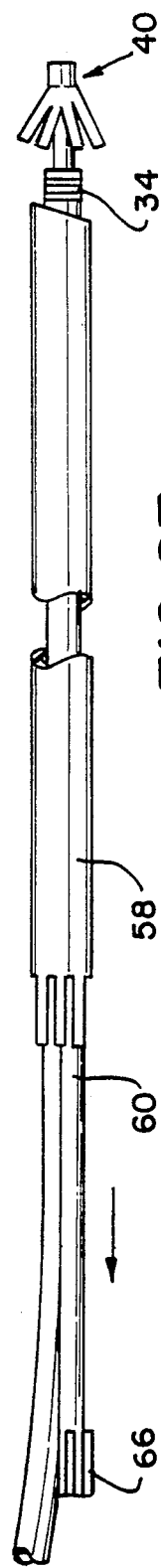
FIG. 2E illustrates removal of the carrier from the canula.
Figure 2F:
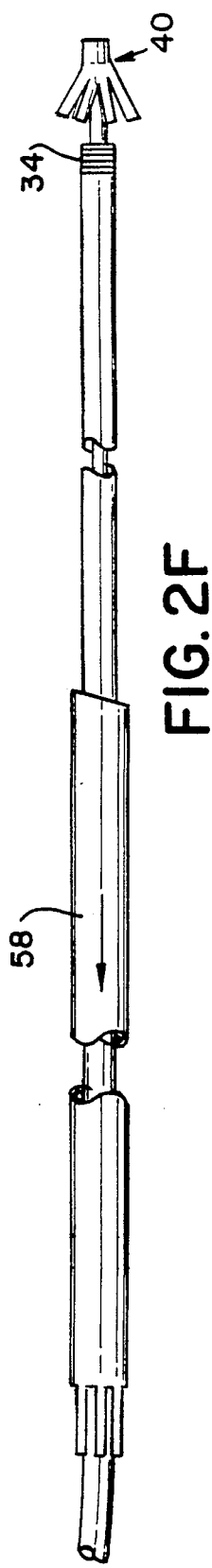
FIG. 2F illustrates removal of the canula from the implanted electrode.

With reference to FIG. 2E, the carrier is removed from the metal sheath. Referring to FIG. 2F, the metal sheath is slid longitudinally off the lead, relying on the anchor 40 to hold the lead at the selected location in the muscle tissue both during removal of the sheath and thereafter.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. An electrode for surgical implantation, the electrode comprising:
    a multistrand wire extending along a helical path;
    a flexible, insulating sheath surrounding and encasing the multistrand wire;
    an insulation-free portion of the multistrand wire being wrapped around a periphery of a terminal end of the sheath to form an electrical contact adapted for transmitting electrical energy to tissue surrounding the electrode.

2. An electrode for surgical implantation, the electrode comprising:
    two multi-filament wires, each encased in insulation and disposed side by side in a helical configuration;
    a flexible sheath surrounding and encasing the two multi-filament wires and the insulation;
    an end portion of the multi-filament wires being wrapped around a periphery of a terminal end of the sheath to form an electrical contact adapted for transmitting electrical energy to tissue surrounding the electrode.

3. An electrode adapted for transmitting electrical energy to surrounding tissue after surgical implantation, the electrode comprising:
    an electrical conductor wound around a hollow core with gaps between adjacent windings;
    a flexible, insulating sheath surrounding and encasing the electrical conductor;
    a portion of the electrical conductor being wrapped around a periphery of a terminal end of the sheath to form an electrical contact;
    a shaft of thermoplastic material in the hollow core and conforming with gaps between windings of the electrical conductor; and,
    an anchor adapted for anchoring the electrode to tissue within which it is implanted, the anchor being connected with the thermoplastic shaft.

4. The electrode as set forth in claim 3 wherein the anchor includes a plurality of polymeric barbs, the barbs being sufficiently strong to anchor the electrode and sufficiently resilient so as to yield and permit extraction of the electrode.

5. The electrode as set forth in claim 4 wherein the anchor barbs and shaft are constructed of polypropylene.

6. An electrode whose terminal end is implantable into tissue, the electrode comprising:
    an insulated electrical conductor wound around an open core;
    a flexible, biocompatible sheathing encasing the electrical conductor, which sheathing terminates adjacent an electrode terminal end;
    an anchor means having a thermoplastic shaft extending therefrom, the anchor shaft being received in the open core and thermally connected to the electrical conductor adjacent the terminal end;
    an uninsulated length of the electrical conductor being wrapped around a periphery of the sheathing adjacent the terminal end.

7. An electrode whose terminal end is implantable into tissue, the electrode comprising:
    two lengths of multifilament wire, each sheathed in a biocompatible insulation wrapped with gaps between adjacent windows around a hollow core, the wires being electrically connected with an exposed electrical conductive surface adjacent a terminal end of the electrode adapted for conducting charge into the tissue within which the electrode is implanted;
    an anchor means having a thermoplastic shaft extending therefrom, the anchor shaft being thermally deformed into the gaps.

8. The electrode as set forth in claim 7 wherein the exposed conductive surface extends along a peripheral surface of the sheath.

9. An electrode whose terminal end is implantable into tissue, the electrode comprising:
    an electrical conductor wrapped about an open core and electrically connected with an exposed electrical conductive surface adjacent a terminal end of the electrode;
    an anchor having a thermoplastic shaft extending therefrom, the anchor shaft being received in the open core and thermally connected to the electrical conductor adjacent the terminal end, the anchor having a plurality of flexible tines that are connected with the anchor shaft.

10. The electrode as set forth in claim 9 wherein the shaft and tines are constructed of polypropylene.

11. A method of inserting an electrode which has an anchor and an exposed electrical contact surface adjacent a terminal end thereof into muscle tissue, the method comprising:
    inserting a probe into muscle tissue to select a point to which the electrical contact surface is to be inserted;
    inserting a sheath over the probe;
    removing the probe from the sheath and inserting the electrode into the sheath;
    advancing the electrode through the sheath with a carrier until the electrical contact surface is at the selected insertion point;
    removing the carrier from the sheath; and,
    removing the sheath from the electrode while the anchor holds the electrode in the muscle tissue.

12. An electrode whose terminal end is implantable into tissue, the electrode comprising:
    an electrical conductor wound in a generally spiral configuration;
    a flexible, insulating sheath having a generally cylindrical outer surface that surrounds and encases the spiral wound electrical conductor;
    an uninsulated length of the electrical conductor being wrapped around the cylindrical periphery of the sheath adjacent a terminal end thereof, which uninsulated length is adapted to transmit electrical energy to adjacent tissue.

13. The electrode as set forth in claim 12 wherein the conductor is wound in loops around a hollow core with gaps between adjacent loops.

14. The electrode as set forth in claim 13 further including an anchor adapted for anchoring the electrode to tissue within which it is implanted, the anchor being connected with the terminal end.

15. An electrode adapted for surgical implantation, the electrode comprising:

an electrical conductor extending along a spiral path, the electrical conductor being electrically connected with an electrically conductive surface adjacent an electrode terminal end, which conductive surface is adapted to conduct charge into surrounding tissue a flexible, insulating sheath having a generally cylindrical outer surface that surrounds and encases the electrical conductor;

a thermoplastic shaft received within and affixed to the spiral electrical conductor adjacent the terminal end, the shaft extending beyond a terminal end of the sheath and the electrically conductive surface;

an anchor connected with the shaft having at least one outward extending anchoring projection, the anchoring projection being adapted to engage adjacent tissue and anchor the electrode against movement relative to the adjacent tissue.

* * * * *